United States Patent
Liu et al.

(10) Patent No.: US 11,490,872 B2
(45) Date of Patent: Nov. 8, 2022

(54) C-ARM IMAGING SYSTEM AND METHOD

(71) Applicant: GE Precision Healthcare LLC, Wauwatosa, WI (US)

(72) Inventors: James Zhengshe Liu, Salt Lake City, UT (US); Christopher Welsh, Lehi, UT (US)

(73) Assignee: GE Precision Healthcare LLC, Wauwatosa, WI (US)

(*) Notice: Subject to any disclaimer, the term of this patent is extended or adjusted under 35 U.S.C. 154(b) by 186 days.

(21) Appl. No.: 16/999,482

(22) Filed: Aug. 21, 2020

(65) Prior Publication Data

US 2022/0054102 A1  Feb. 24, 2022

(51) Int. Cl.
*G01D 18/00* (2006.01)
*H05G 1/44* (2006.01)
(Continued)

(52) U.S. Cl.
CPC ............ *A61B 6/582* (2013.01); *A61B 6/4441* (2013.01); *A61B 6/5205* (2013.01); *A61B 6/542* (2013.01); *H01J 35/025* (2013.01)

(58) Field of Classification Search
CPC ...... H01J 35/025; A61B 6/5205; A61B 6/582; A61B 6/4441; A61B 6/542; A61B 6/482; A61B 6/54; A61B 6/032; A61B 6/545; A61B 6/481; A61B 6/037; A61B 6/0407; A61B 6/5211; A61B 6/5258; A61B 5/0245; A61B 6/504; A61B 6/541; A61B 6/02; A61B 6/4233; A61B 6/04; A61B 6/4208; A61B 6/5217; A61B 6/585; A61B 6/583; A61B 6/4085; A61B 6/488; A61B 6/544;
(Continued)

(56) References Cited

U.S. PATENT DOCUMENTS 6,175,614 B1   1/2001   Jensen
6,373,915 B1   4/2002   Fujimoto
(Continued)

OTHER PUBLICATIONS

Probabilistic Air Segmentation and Sparse Regression Estimated Pseudo CT for PET/MR Attenuation Correction; Radiology: vol. 275: No. 2—May 2015; https://www.ncbi.nlm.nih.gov/pmc/articles/PMC4409527/pdf/radiol.14140810.pdf; pp. 562-569.

*Primary Examiner* — Irakli Kiknadze

(57) ABSTRACT

A system for imaging an object includes an X-ray source operative to transmit X-rays through the object and a detector to receive the X-ray energy of the X-rays after passing through the object and to generate corresponding object X-ray intensity. The system also includes a controller to measure a detector entrance dose with no object being placed on the X-ray beam path and determine a relationship between an X-ray tube electrical parameter and the detector entrance dose. The controller further determines a relationship between the X-ray tube electrical parameter, the detector entrance dose and a detector average pixel intensity and obtains a normalized air map as a function of the X-ray tube electrical parameter based on calibration image data. The controller also generates an air map based on the normalized air map, the detector entrance dose and the detector average pixel intensity and reconstructs an image of the object based on the air map and the measured object X-ray intensity.

20 Claims, 5 Drawing Sheets

(51) Int. Cl.
  *A61B 6/00* (2006.01)
  *H01J 35/02* (2006.01)

(58) Field of Classification Search
  CPC .............. G06T 7/0012; G06T 11/006; G06T 2207/10081; G06T 2211/424; G06T 2211/421; G06T 2207/30101; G06T 11/005; G06T 7/0016; G06T 11/003; G06T 11/008; G06T 2207/10116; G01N 23/046; G01N 2223/419; G01N 2223/612; A61N 5/1071; A61N 5/1067; A61N 5/1075; A61N 2005/1076; G16H 30/40; G16H 50/50; G16H 20/40
  USPC .......................................... 378/207, 108, 62
  See application file for complete search history.

(56) References Cited

U.S. PATENT DOCUMENTS

| | | | |
|---|---|---|---|
| 6,574,493 B2 | 6/2003 | Rasche | |
| 6,666,579 B2 | 12/2003 | Jensen | |
| 7,197,105 B2 | 3/2007 | Katsevich | |
| 7,597,477 B1 | 10/2009 | Hosseinian | |
| 7,778,392 B1 | 8/2010 | Berman | |
| 7,856,080 B2 | 12/2010 | Klingenbeck-Regn | |
| 7,856,084 B2 | 12/2010 | Pasini | |
| 8,107,592 B2 | 1/2012 | Berman | |
| 8,121,250 B2 | 2/2012 | Dafni | |
| 8,213,565 B2 | 7/2012 | Boese | |
| 8,249,213 B2 | 8/2012 | Noordhoek | |
| 8,285,014 B2 | 10/2012 | Lauritsch | |
| 8,447,009 B2 | 5/2013 | Flohr | |
| 8,494,245 B2 | 7/2013 | Liao | |
| 8,644,576 B2 | 2/2014 | Zheng | |
| 8,724,881 B2 | 5/2014 | Zheng | |
| 8,781,243 B2 | 7/2014 | Chen | |
| 8,934,693 B2 | 1/2015 | Grbic | |
| 9,076,237 B2 | 7/2015 | Chen | |
| 9,292,917 B2 | 3/2016 | Grbic | |
| 9,373,159 B2 | 6/2016 | Amroabadi | |
| 9,384,546 B2 | 7/2016 | Zheng | |
| 9,414,799 B2 | 8/2016 | Mistretta | |
| 10,417,765 B2 | 9/2019 | Saalbach | |
| 10,524,865 B2 | 1/2020 | Trousset | |
| 2008/0075349 A1* | 3/2008 | Ritter | H04N 5/32 378/207 |
| 2009/0076373 A1 | 3/2009 | Maschke | |
| 2009/0198121 A1 | 8/2009 | Hoheisel | |
| 2009/0281452 A1 | 11/2009 | Pfister | |
| 2010/0036239 A1 | 2/2010 | Klingenbeck-Regn | |
| 2015/0038862 A1 | 2/2015 | Gijsbers | |
| 2015/0282779 A1 | 10/2015 | Deuerling-Zheng | |
| 2016/0113617 A1* | 4/2016 | Herrmann | A61B 6/42 378/207 |
| 2016/0166329 A1 | 6/2016 | Langan | |
| 2016/0183908 A1* | 6/2016 | Hayashida | A61B 6/4291 378/207 |
| 2017/0039734 A1 | 2/2017 | Langan | |
| 2017/0215818 A1 | 8/2017 | De Man | |
| 2019/0187308 A1 | 6/2019 | Liu | |
| 2019/0246998 A1 | 8/2019 | Liu | |
| 2019/0269378 A1 | 9/2019 | Lautenschlaeger | |
| 2021/0204901 A1* | 7/2021 | Matsuda | A61B 6/4411 |

* cited by examiner

C-ARM IMAGING SYSTEM AND METHOD

BACKGROUND

The subject matter disclosed herein relates to X-ray imaging systems having C-arms and, more particularly, to air calibration of X-ray imaging systems in 3D image reconstruction.

Medical diagnostic imaging systems generate images of an object, such as a patient, for example, through exposure to an energy source, such as X-rays passing through a patient, for example. The generated images may be used for many purposes. Often, when a practitioner takes X-rays of a patient, it is desirable to take several X-rays of one or more portions of the patient's body from a number of different positions and angles, and preferably without needing to frequently reposition the patient. To meet this need, C-arm X-ray system has been developed. The term C-arm generally refers to an X-ray imaging device having a rigid and/or articulating structural member having an X-ray source and an image detector assembly that are each located at an opposing end of the structural member so that the X-ray source and the image detector face each other. The structural member is typically "C" shaped and so is referred to as a C-arm. In this manner, X-rays emitted from the X-ray source can impinge on the image detector and provide an X-ray image of the object or objects that are placed between the X-ray source and the image detector.

The C-arm X-ray system includes various electrical and optical components which have gain and offset values suitable for only a certain range of operating conditions. The gain drift of the electrical and optical components introduces undesirable artifacts in the final image produced by the C-arm X-ray system. Therefore, to remove these artifacts, it is necessary to calibrate the C-arm X-ray system regularly. Further, even without drift, the calibration is needed to establish the relationship between the X-ray technique being used and the image detector output. Moreover, the calibration helps in compensating for the non-ideal response of the X-ray tube and the X-ray detector.

BRIEF DESCRIPTION

In accordance with an embodiment of the present technique, a system for imaging an object is provided. The system includes an X-ray source operative to transmit X-rays through the object and a detector operative to receive the X-ray energy of the X-rays after having passed through the object and to generate corresponding object X-ray intensity. The system further includes a controller operative to measure a detector entrance dose with no object being placed on the X-ray beam path and to determine a relationship between an X-ray tube electrical parameter and the detector entrance dose. The controller is further operative to determine a relationship between the X-ray tube electrical parameter, the detector entrance dose and a detector average pixel intensity and to obtain a normalized air map as a function of the X-ray tube electrical parameter based on calibration image data. The controller is also operative to generate an air map based on the normalized air map, the detector entrance dose and the detector average pixel intensity and to reconstruct an image of the object based on the air map and the measured object X-ray intensity.

In accordance with another embodiment of the present technique, a method for imaging an object is provided. The method includes transmitting X-rays from an X-ray source to the object and acquiring measurement data related to the object. The method also includes measuring a detector entrance dose with no object being placed on the X-ray beam path and determining a relationship between an X-ray tube electrical parameter and the detector entrance dose. The method further includes determining a relationship between the X-ray tube electrical parameter, detector entrance dose and a detector average pixel intensity and obtaining a normalized air map as a function of the X-ray tube electrical parameter based on calibration image data. Finally, the method includes generating an air map based on the normalized air map, the detector entrance dose and the detector average pixel intensity and reconstructing an image of the object based on the air map and the measurement data related to the object.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments. Furthermore, the terms "circuit"

and "circuitry" and "controller" may include either a single component or a plurality of components, which are either active and/or passive and are connected or otherwise coupled together to provide the described function.

Figure 1:
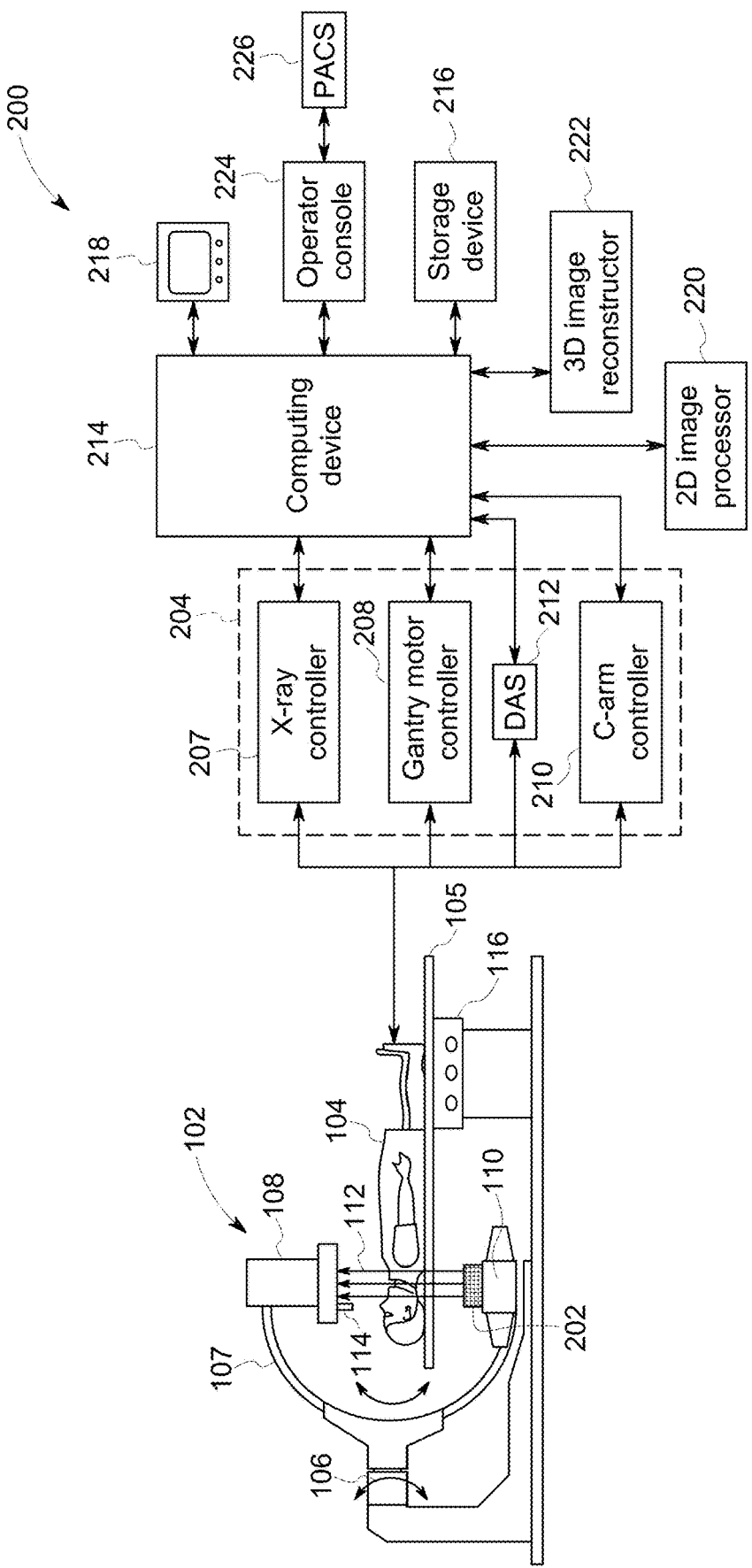
FIG. 1 is a schematic drawing of a radiologic imaging system in accordance with aspects of the present approach.

FIG. 1 illustrates an exemplary radiologic imaging system 200, for example, for use in interventional medical procedures. In one embodiment, the system 200 may include a C-arm radiography system 102 configured to acquire projection data from one or more view angles around a subject, such as a patient 104 positioned on an examination table 105 for further analysis and/or display. To that end, the C-arm radiography system 102 may include a gantry 106 having a mobile support such as a movable C-arm 107 including at least one radiation source 110 such as an X-ray tube and a detector 108 positioned at opposite ends of the C-arm 107. In exemplary embodiments, the radiography system 102 can be an X-ray system, a positron emission tomography (PET) system, a computerized tomosynthesis (CT) system, an angiographic or fluoroscopic system, and the like or combination thereof, operable to generate static images acquired by static imaging detectors (e.g., CT systems, MRI systems, etc.) prior to a medical procedure, or real-time images acquired with real-time imaging detectors (e.g., angioplastic systems, laparoscopic systems, endoscopic systems, etc.) during the medical procedure, or combinations thereof. Thus, the types of acquired images can be diagnostic or interventional.

In certain embodiments, the radiation source 110 may include multiple emission devices, such as one or more independently addressable solid-state emitters arranged in one or multi-dimensional field emitter arrays, configured to emit the X-ray beams 112 towards the detector 108. Further, the detector 108 may include a plurality of detector elements that may be similar or different in size and/or energy sensitivity for imaging a region of interest (ROI) of the patient 104 at a desired resolution. In one embodiment, a dosimeter 114 is provided near the detector 108 to measure the X-ray dose per frame at the entrance of the detector 108.

In certain embodiments, the C-arm 107 may be configured to move along a desired scanning path for orienting the X-ray source 110 and the detector 108 at different positions and angles around the patient 104 for acquiring information for 3D imaging of dynamic processes. Accordingly, in one embodiment, the C-arm 107 may be configured to rotate about a first axis of rotation. Additionally, the C-arm 107 may also be configured to rotate about a second axis in an angular movement with a range of about plus or minus 60 degrees relative to the reference position. In certain embodiments, the C-arm 107 may also be configured to move forwards and/or backwards along the first axis and/or the second axis.

Accordingly, in one embodiment, the C-arm system 102 may include control circuitry 204 configured to control the movement of the C-arm 107 along the different axes based on user inputs and/or protocol-based instructions. To that end, in certain embodiments, the C-arm system 102 may include circuitry such as tableside controls 116 that may be configured to provide signals to the control circuitry 204 for adaptive and/or interactive control of imaging and/or processing parameters using various input mechanisms. The imaging and/or processing parameters, for example, may include display characteristics, X-ray technique and frame rate, scanning trajectory, and gantry motion and/or position.

In certain embodiments, the detector 108 may include a plurality of detector elements 202, for example, arranged as a 2D detector array for sensing the projected X-ray beams 112 that pass through the patient 104. In one embodiment, the detector elements 202 produce an electrical signal representative of the intensity of the impinging X-ray beams 112, which in turn, can be used to estimate the attenuation of the X-ray beams 112 as they pass through the patient 104. In another embodiment, the detector elements 202 determine a count of incident photons in the X-ray beams 112 and/or determine corresponding energy.

Particularly, in one embodiment, the detector elements 202 may acquire electrical signals corresponding to the generated X-ray beams 112 at a variety of angular positions around the patient 104 for collecting a plurality of radiographic projection views for construction of X-ray images, such as to form fluoro image(s). To that end, control circuitry 204 for the system 200 may include a control mechanism configured to control position, orientation and/or rotation of the gantry 106, the C-arm 107 and/or the components mounted thereon in certain specific acquisition trajectories.

In certain embodiments, the X-ray source 110 and the detector 108 for interventional imaging may be controlled using an X-ray controller 207 in the control mechanism 204, where the X-ray controller 207 is configured to provide power and timing signals to the radiation source 110 for controlling X-ray exposure during imaging. Further, the control mechanism 204 may also include a gantry motor controller 208 that may be configured to control the rotational speed, tilt, view angle, and/or position of the gantry 106. In certain embodiments, the control mechanism 204 also includes a C-arm controller 210, which in concert with the gantry motor controller 208, may be configured to move the C-arm 107 for real-time imaging of dynamic processes.

In one embodiment, the control mechanism 204 may include a data acquisition system (DAS) 212 for acquiring the projection data from the detector elements 206 and processing the data for image reconstruction by 2D image processor 220, for reconstructing high-fidelity 2D images in real-time for use during the interventional procedure, and/or 3D image processor/reconstructor 222, for generating 3D cross-sectional images (or 3D volumes), and subsequent illustration of the images on display 218. Moreover, in certain embodiments, the data obtained by the DAS 212 may be input to a computing device 214. Alternatively, in certain embodiments, the computing device 214 may store the projection data in a storage device 216, such as a hard disk drive, a floppy disk drive, a compact disk-read/write (CD-R/W) drive, a Digital Versatile Disc (DVD) drive, a flash drive, or a solid-state storage device for further evaluation.

In one embodiment, the system 200 may include an operator console 224 that may be configured to allow selection and display of scanning modes, FOV, prior exam data, and/or intervention path. The operator console 224 may also allow on-the-fly access to 2D and 3D scan parameters and selection of an ROI for subsequent imaging, for example, based on operator and/or system commands.

Further, in certain embodiments, the system 200 may be coupled to multiple displays, printers, workstations, a picture archiving and communications system (PACS) 226 and/or similar devices located either locally or remotely, for example, within an institution or hospital, or in an entirely different location via communication links in one or more configurable wired and/or wireless networks such as a hospital network and virtual private networks.

In operation, during a 3D scan of the object (e.g., patient), the X-ray detector measures the image data to generate an actual object X-ray intensity, $I_t$ after X-rays pass through the object. The 3D image processor/reconstructor 222 utilizes this actual object X-ray intensity $I_t$ to generate the 3D image of the object. This actual object intensity $I_t$ is related to the unattenuated X-ray intensity, $I_0$, along the path from the X-ray source to the X-ray detector pixel by the Beer-Lambert law:

$$I_t = I_0 \cdot e^{-\mu t} \qquad \text{Eq. 1}$$

where t is the thickness of the object and μ is the attenuation coefficient of the object.

In accordance with an embodiment of the present technique, an air calibration is performed on the C-arm radiography system 102 by measuring the X-ray intensity with no object in the path of the X-ray beam 112 i.e., unattenuated X-ray intensity $I_0$. The air calibration compensates for the X-ray field non-uniformity, X-ray detector pixel gain including analog to digital (A/D) converter gain non-uniformity, as well as the tube-detector alignment variation from view to view. The outcome of the calibration is a series of two-dimensional maps called as an air map which represents the unattenuated X-ray intensity $I_0$. In general, the air calibration is designed to obtain the unattenuated intensity, $I_0$, to normalize the scan data to the unobstructed beam intensity, which is used to determine the amount of attenuation caused by an object in the beam path. Based on the determined unattenuated intensity, $I_0$, and measured actual object X-ray intensity $I_t$, the X-ray attenuation caused by an object in the beam may be calculated. The X-ray attenuation of the object is further used to generate or reconstruct the 3D image of the object.

Figure 2:
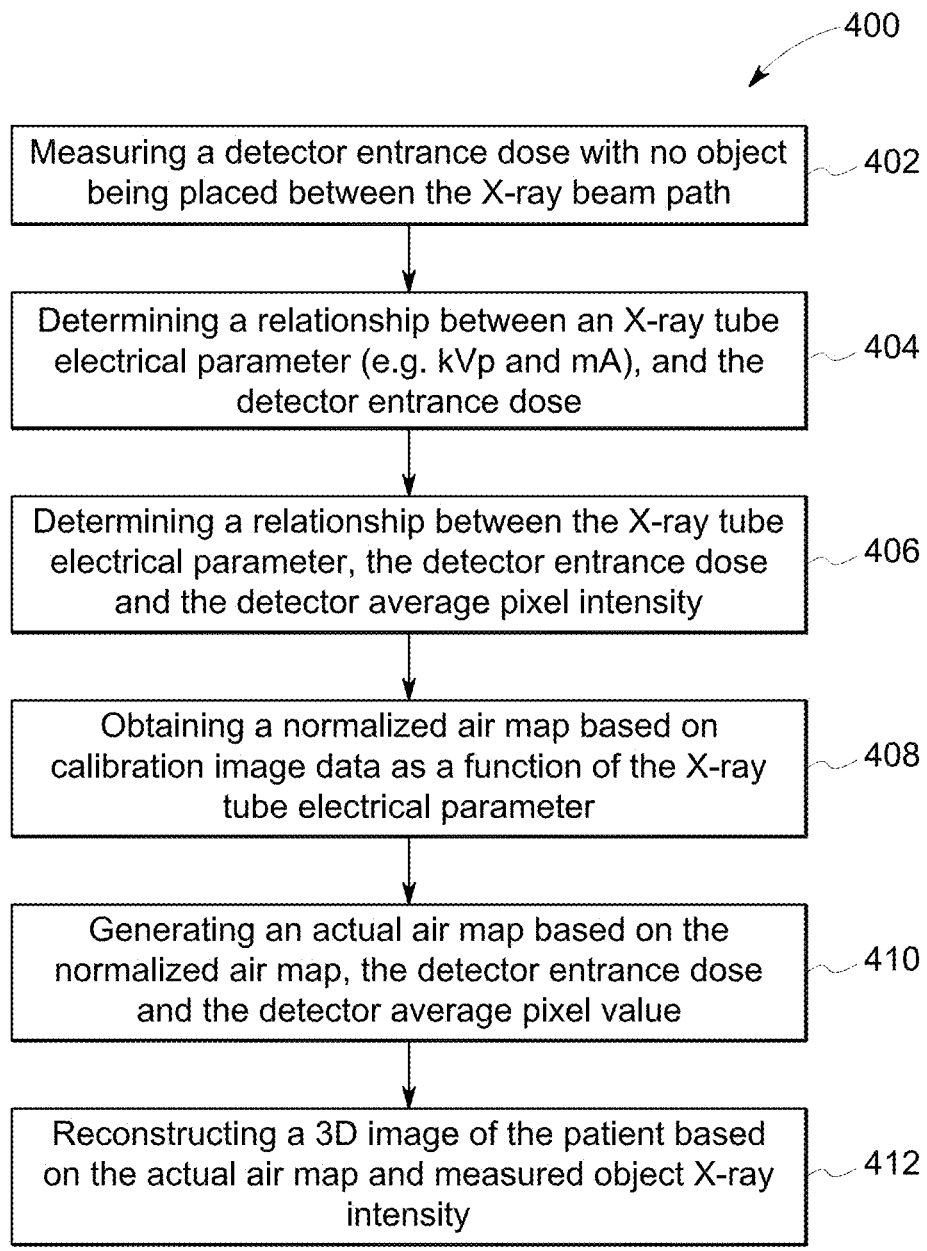
FIG. 2 is flow chart of depicting a method for imaging an object, in accordance with aspects of the present approach.

FIG. 2 illustrates a flow chart 400 depicting an exemplary method for imaging an object in accordance with an embodiment of the present technique. In one embodiment, the method of flow chart 400 may be implemented in computing device 214 of FIG. 1. Embodiments of the exemplary method may include computer executable instructions on a computing system or a processor. Generally, computer executable instructions may include routines, programs, objects, components, data structures, procedures, modules, functions, and the like that perform particular functions or implement particular abstract data types. Embodiments of the exemplary method including computer executable instructions may also be practiced in a distributed computing environment where optimization functions are performed by remote processing devices that are linked through a wired and/or wireless communication network. In the distributed computing environment, the computer executable instructions may be located in both local and remote computer storage media, including memory storage devices.

Embodiments of the present method describe techniques for enhanced imaging of high-quality 3D cross-sectional images using a C-arm system 102. To that end, at step 402, a detector entrance dose is measured with no object being placed on the path of the X-ray beam 112. In one embodiment, the detector entrance dose is measured by dosimeter 114 placed at the entrance of the detector 108. In one embodiment, the dosimeter measures the detector entrance dose in a unit of microgray/frame (μGy/Frame).

At step 404, a relationship between an X-ray tube electrical parameter and the detector entrance dose is determined based on the measured dose data. The X-ray tube electrical parameter includes the electrical parameter applied to the X-ray tube such as a tube voltage, a tube current or combinations thereof. As will be appreciated by those skilled in the art, the unit for tube voltage is Kilovoltage peak (kVp) and the unit for tube current is milliampere (mA). In general, the tube voltage controls energy and quality of the X-ray beam produced by the X-ray tube whereas the tube current controls the quantity of the X-ray beam.

Figure 3:
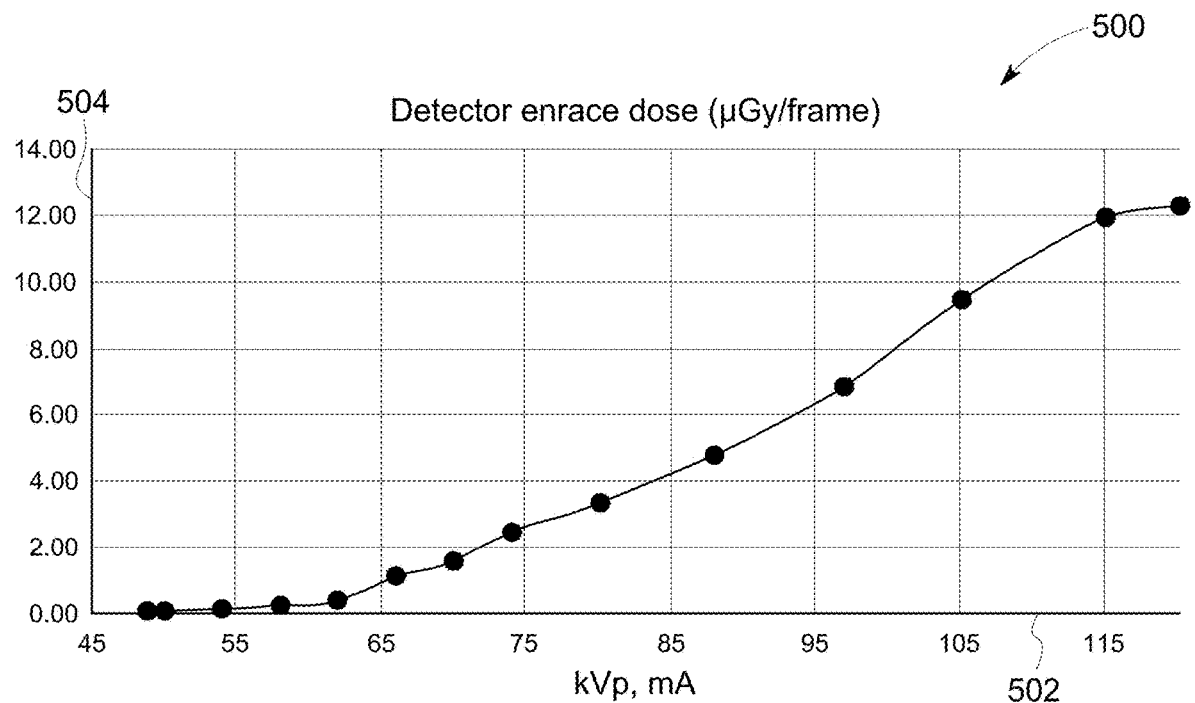
FIG. 3 is a graphical plot depicting a relationship between an X-ray tube electrical parameter and a detector entrance dose, in accordance with aspects of the present approach.

FIG. 3 shows a graphical plot 500 of an exemplary relationship between an X-ray tube electrical parameter and a detector entrance dose. A horizontal axis 502 of the plot 500 represents a tube voltage in kVp with a given tube current in mA whereas a vertical axis 504 represents detector entrance dose in μGy/Frame. In general, as the tube voltage of the X-ray tube is increased the detector entrance dose at the entrance of the detector entrance is measured by the dosimeter at the surface of the detector.

It should be noted that in one embodiment, the detector entrance dose may be measured while both the tube voltage and the tube current are being changed. In which case, the detector entrance dose becomes the function of both tube voltage and tube current. The tube voltage and the tube current may be changed as a predefined pair in accordance with a 3D automatic brightness system (ABS) table. The 3D ABS is used to keep the brightness of the displayed image at a constant level during X-ray examinations. In one embodiment, the 3D ABS also adjusts a digital gain to adjust the brightness of the image. The kV and mA may be adjusted as a pair depending on the patient and the part of the anatomy of the patient being examined. Note that the tube current mA needs to be adjusted such that the pixel values are around the middle of the dynamic range of the detector to avoid the non-linearity near the saturation. In such a case, the horizontal axis 502 can represent a tube voltage and tube current (kVp/mA) pair instead of the tube voltage (kVp) which is fixed for the given tube current (mA).

In one embodiment, a linear interpolation of the measurement points of the plot 500 in FIG. 3 is performed to find out the relationship between the X-ray tube electrical parameter and the detector entrance dose. For example, let the kVp be the actual kVp in the projection and let kVp(n) and kVp(n+1) be the two consecutive kVp values obtained during the air calibration i.e., n is an index number. Also assume that D(n) and D(n+1), respectively, are the two detector entrance dose values in μGy/frame corresponding to kVp(n) and kVp(n+1) obtained from the air calibration. The detector entrance dose D in μGy/frame corresponding to kVp in the projection is then given by the following linear interpolation:

$$D = D(n+1) + \frac{[D(n+1) - D(n)] \cdot [kVp - kVp(n+1)]}{kVp(n+1) - kVp(n)}, \qquad \text{Eq. 2}$$

Turning back to FIG. 2, at step 406, a relationship between the X-ray tube electrical parameter, the detector entrance dose and a detector average pixel intensity as measured by the detector 108 when no object is placed on the X-ray beam path is determined. The average pixel intensity is calculated by averaging pixel values of all the detector elements. In one embodiment, the average pixel value is determined by a central region of interest (e.g., 512×512 pixels, specifically, out of a 1536×1536 pixel image) instead of using all the pixels from the detector since the X-ray beam is collimated in the corners (creating a "squircle") For a given X-ray spectrum, the average pixel intensity of an X-ray detector is known to be linearly proportional to the detector entrance dose as measured by the dosimeter 114. In other words, the detector pixel intensity is linearly proportional to the detector entrance dose for any given X-ray tube electrical parameters such as tube voltages kVps. Therefore, for a given tube voltage kVp, we can establish the relationship between the tube voltage kVp and the average detector pixel intensity by dividing the average detector pixel intensity by the detector entrance dose and the ABS digital gain at the time of the measurement of the average detector pixel intensity.

Figure 4:
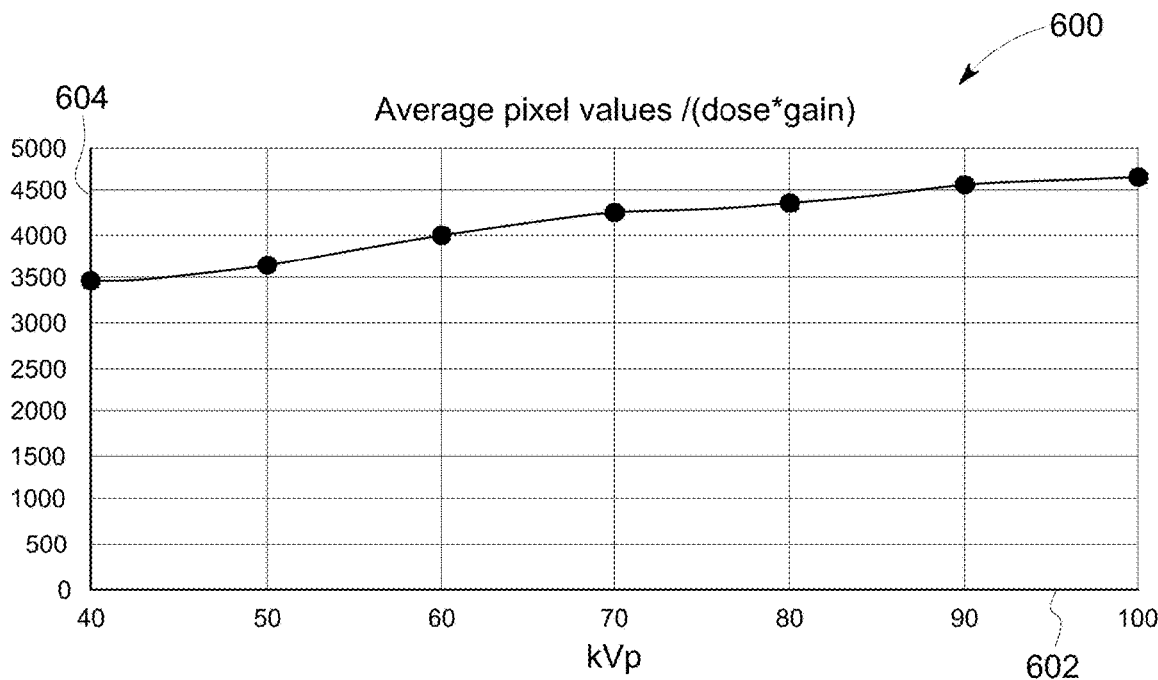
FIG. 4 is a graphical plot depicting a relationship between the X-ray tube electrical parameter and an average pixel value normalized by the detector entrance dose, in accordance with an embodiment of the present technique.

FIG. 4 shows a graphical plot 600 of an exemplary relationship between the X-ray tube electrical parameter and an average pixel value normalized by detector entrance dose. A horizontal axis 602 of the plot 600 represents a tube voltage in kVp whereas a vertical axis 604 represents average pixel value with unity dose in pixel counts. The average pixel value with unity dose is determined by dividing the average pixel value by the detector entrance dose and the ABS digital gain at the time of the measurement of the average detector pixel intensity.

In one embodiment, the plot 600 between the X-ray tube electrical parameter with unity dose as well as unity gain and average pixel value is represented in terms of a mathematical equation. For example, as earlier, let the kVp be the actual kVp in the projection and let kVp(n) and kVp(n+1) be the two consecutive kVp values obtained during the air calibration. Also assume that P(n) and P(n+1), respectively, are the two detector average pixel values corresponding to kVp(n) and kVp(n+1) obtained from the air calibration. The detector average pixel value P for the projection corresponding to kVp in the projection is then given by the following linear interpolation:

$$P = P(n+1) + \frac{[P(n+1) - P(n)] \cdot [kVp - kVp(n+1)]}{kVp(n+1) - kVp(n)}, \quad \text{Eq. 3}$$

Turning back to FIG. 2, at step 408, a normalized air map based on calibration image data is obtained as a function of the X-ray tube electrical parameter. An air map is basically an X-ray intensity map proportional to the unattenuated X-ray intensity $I_0$. In general, based on the detector entrance dose D (from Eq. 2) and the average detector pixel value P (from Eq. 3), we can obtain the average pixel value for any triumvirate {kVp, mA, K} defined by the 3D ABS table, where the kVp is the X-ray tube voltage, mA is the X-ray tube current and K is the ABS digital gain. However, in order to include the pixel to pixel variation due to detector pixel gain including the A/D gain, detector scintillator non-uniformity, and X-ray field non-uniformity, we also need to obtain the two-dimensional air map or X-ray intensity map for the X-ray detector.

Figure 5:
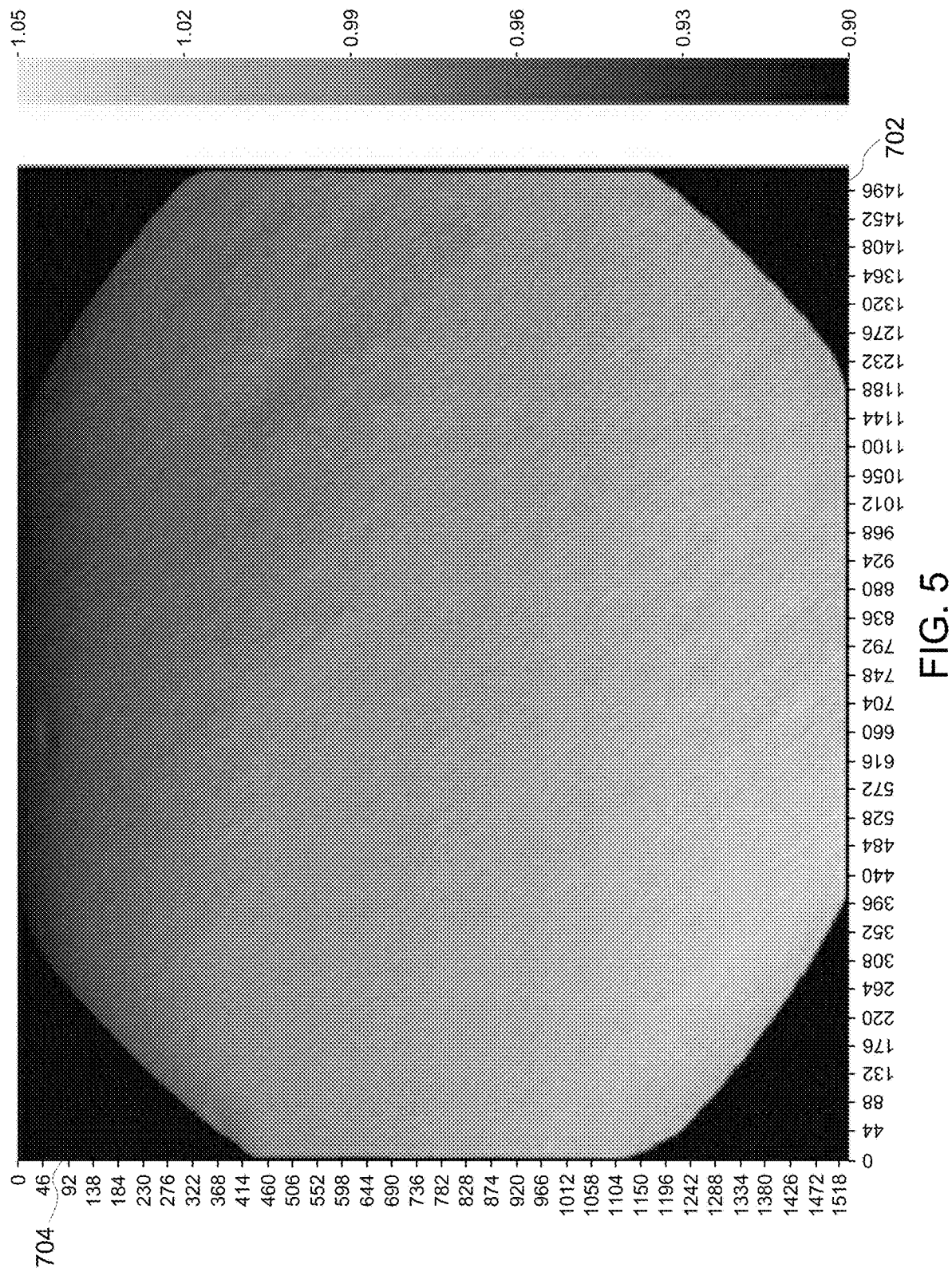
FIG. 5 is a graphical plot depicting a normalized air map, in accordance with an embodiment of the present technique.

FIG. 5 shows a graphical plot 700 of a normalized air map with respect to the average pixel value for X-ray tube voltage equal to 80 kVp. A horizontal axis 702 of the plot 700 and a vertical axis 704 of the plot represents the coordinates of the image pixels respectively in terms of the location of the pixel. To obtain the normalized air map, for a given tube voltage kVp, the tube current mA is adjusted such that the detector output pixel values are around the middle of the detector measurement range when no object is placed on the X-ray beam path. A sequence of calibration images (i.e., calibration image data) is acquired with the same operating condition. The resulting images are firstly averaged to generate one air image with reduced image noise. As will be appreciated by those skilled in the art, image averaging works on the assumption that the noise in the image is truly random. This way, random fluctuations in the image data gradually even out as one averages more and more images. Then the average pixel value of the obtained air image is calculated. Finally, the normalized air map is obtained by the average pixel value divided by the air image.

In one embodiment, the normalized air map may be represented in terms of a mathematical equation. For example, as earlier, let the kVp be the actual kVp in the projection and let kVp(n) and kVp(n+1) be the two consecutive kVp values obtained during the air calibration. Also assume that $\bar{a}_{i,j}^{\{kVp(n)\}}$ and $\bar{a}_{i,j}^{\{kVp(n+1)\}}$, respectively, are the two normalized air maps corresponding to kVp(n) and kVp(n+1) obtained from the air calibration. The normalized air map $\bar{a}_{i,j}^{\{kVp\}}$ corresponding to kVp of the projection is then given by the following linear interpolation:

$$\bar{a}_{i,j}^{\{kVp\}} = \bar{a}_{i,j}^{\{kVp(n+1)\}} + \frac{\left[\bar{a}_{i,j}^{\{kVp(n+1)\}} - \bar{a}_{i,j}^{\{kVp(n)\}}\right] \cdot [kVp - kVp(n+1)]}{kVp(n+1) - kVp(n)}, \quad \text{Eq. 4}$$

Turning back to FIG. 2, at step 410, an air map is generated based on the detector entrance dose D (from Eq. 2), the average detector pixel value P (from Eq. 3) and the normalized air map $\bar{a}_{i,j}^{\{kVp\}}$ (from Eq. 4) using the following equation:

$$I_0(i,j) = D \times P \times \bar{a}_{i,j}^{\{kVp\}} \quad \text{Eq. 5}$$

where $I_0(i, j)$ is the air map, and $(i, j)$ are the coordinates of the image pixels. Finally, at step 412, a 3D image of the subject is reconstructed based on the air map and the measured object X-ray intensity $I_t(i, j)$. Together with the actual image data $I_t(i,j)$, the air map $I_0(i, j)$ is used to determine the x-ray attenuation $\mu t(i,j)$:

$$\mu t(i, j) = \ln\left[\frac{I_0(i, j)}{I_t(i, j)}\right] \quad \text{Eq. 6}$$

The x-ray attenuation $\mu t(i, j)$ is then further used to generate the reconstructed 3D image by the 3D image processor/reconstructor 222 as will be appreciated by those skilled in the art.

Figure 6:
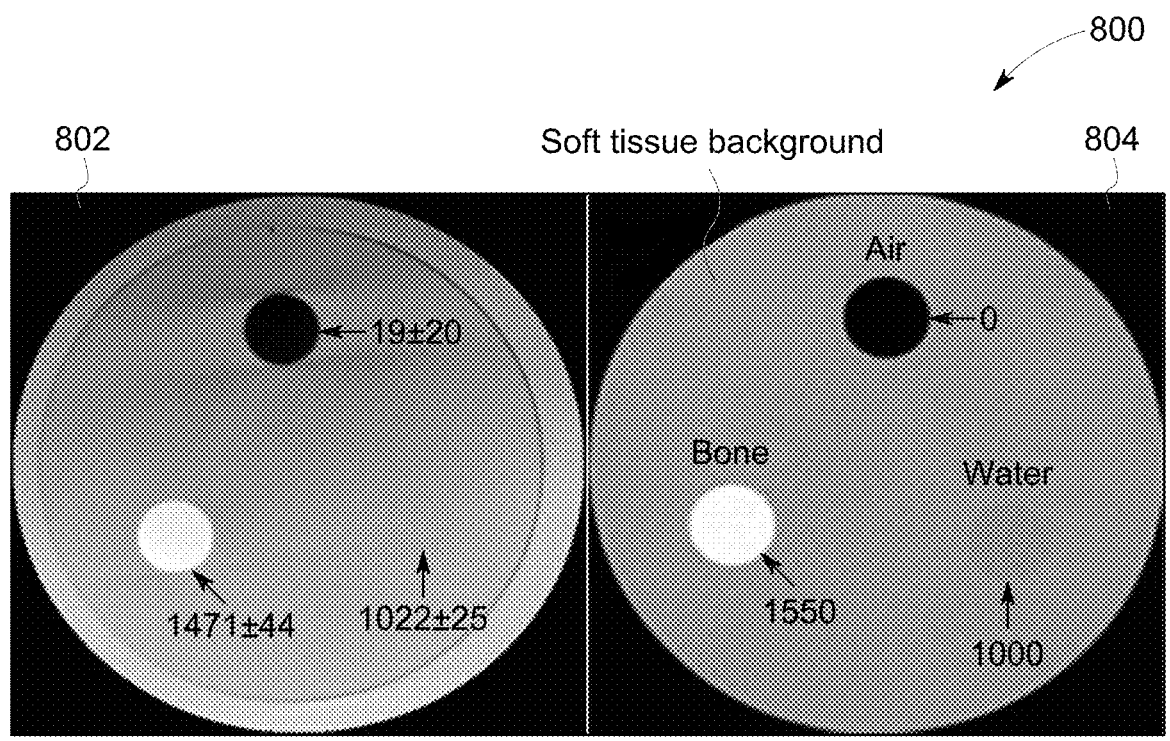
FIG. 6 is a pictorial diagram of a comparison of a reconstructed image and a ground truth image, in accordance with an embodiment of the present technique.

FIG. 6 shows a pictorial diagram 800 of a comparison of a reconstructed image and a ground truth image in accordance with an embodiment of the present technique. In general, the image 802 represents a reconstructed image and the image 804 represents the ground truth image, both with an offset of +1000. In other words, both the reconstructed image and the ground truth image are represented in a "shifted" Hounsfield Units (sHU). As can be seen, the reconstructed image 802 is almost the same as the ground truth image 804. For example, the ground truth image shows the CT number for the bone as 1550, for air as 0 and for water as 1000, whereas the reconstructed image shows the CT numbers for these same elements as 1471, 19 and 1022 respectively.

It may be noted that the foregoing examples, demonstrations, and process steps that may be performed by certain components of the present systems, for example, by the control mechanism 207, the DAS 212, the computing device 214, the processor 220 and/or the image reconstructor 222 may be implemented by suitable code on a processor-based system, such as a general-purpose or special-purpose computer. It may also be noted that different implementations of the present technique may perform some or all of the steps described herein in different orders or substantially concurrently, that is, in parallel.

Additionally, the functions may be implemented in a variety of programming languages, including but not limited to Ruby, Hypertext Preprocessor (PHP), Perl, Delphi, Python, C, C++, or Java. Such code may be stored or adapted for storage on one or more tangible, machine-readable media, such as on data repository chips, local or remote hard disks, optical disks (that is, CDs or DVDs), solid-state drives, or other media, which may be accessed by the processor-based system to execute the stored code.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for imaging an object comprising:
   an X-ray source operative to transmit X-rays through the object;
   a detector operative to receive the X-ray energy of the X-rays after having passed through the object and to generate corresponding object X-ray intensity; and
   a controller operative to:
   measure a detector entrance dose with no object being placed on the X-ray beam path;
   determine a relationship between an X-ray tube electrical parameter and the detector entrance dose;
   determine a relationship between the X-ray tube electrical parameter, the detector entrance dose and a detector average pixel intensity;
   obtain a normalized air map as a function of the X-ray tube electrical parameter based on calibration image data;
   generate an air map based on the normalized air map, the detector entrance dose and the detector average pixel intensity; and
   reconstruct an image of the object based on the air map and the measured object X-ray intensity.

2. The system of claim 1, wherein the X-ray tube electrical parameter comprises a tube voltage, a tube current or combinations thereof.

3. The system of claim 1, wherein the detector entrance dose comprises a plurality of detector entrance dose values corresponding to a plurality of X-ray tube electrical parameter values.

4. The system of claim 3, wherein the controller is operative to determine the relationship between the X-ray tube electrical parameter and the detector entrance dose based on a linear interpolation of the plurality of detector entrance dose values.

5. The system of claim 1, wherein the detector average pixel intensity is divided by the detector entrance dose and a digital gain for determining the relationship between the X-ray tube electrical parameter, the detector entrance dose and the detector average pixel intensity.

6. The system of claim 5, wherein the controller is operative to determine the relationship between the X-ray tube electrical parameter and the detector average pixel intensity based on a linear interpolation of the plurality of average pixel intensity values divided by the detector entrance dose and the digital gain.

7. The system of claim 5, wherein the controller is operative to obtain the normalized air map by dividing the calibration image data of the object with the detector average pixel intensity.

8. The system of claim 7, wherein the calibration image data is obtained by adjusting the X-ray tube electrical parameter such that the calibration image data pixel values are around the middle of the dynamic range of the detector.

9. The system of claim 5, wherein the controller is operative to obtain the normalized air map based on a linear interpolation of data points of the division of calibration image with the detector average pixel intensity.

10. The system of claim 1, wherein the controller is operative to generate the air map based on the following equation:
    where is the air map, D is the detector entrance dose, P is the detector average pixel intensity, (i, j) are the pixel coordinates, kVp is the X-ray tube electrical parameter, and is the normalized air map.

11. The system of claim 10, wherein the controller is operative to reconstruct the image of the object based on the air map and the object X-ray intensity by first determining the x-ray attenuation based on the air map and the object X-ray intensity.

12. A method for imaging an object comprising:
    transmitting X-rays from an X-ray source to the object;
    acquiring measurement data related to the object;
    measuring a detector entrance dose with no object being placed on the X-ray beam path;
    determining a relationship between an X-ray tube electrical parameter and the detector entrance dose;
    determining a relationship between the X-ray tube electrical parameter, detector entrance dose and a detector average pixel intensity;
    obtaining a normalized air map as a function of the X-ray tube electrical parameter based on calibration image data;
    generating an air map based on the normalized air map, the detector entrance dose and the detector average pixel intensity; and
    reconstructing an image of the object based on the air map and the measurement data related to the object.

13. The method of claim 12, wherein the X-ray tube electrical parameter comprises a tube voltage, a tube current or combinations thereof.

14. The method of claim 12, wherein the detector entrance dose comprises a plurality of detector entrance dose values corresponding to a plurality of X-ray tube electrical parameter values.

15. The method of claim 14, wherein determining the relationship between the X-ray tube electrical parameter and the detector entrance dose comprises using a linear interpolation of the plurality of detector entrance dose values.

16. The method of claim 12, wherein the detector average pixel intensity is divided by the detector entrance dose and a digital gain for determining the relationship between the X-ray tube electrical parameter, the detector entrance dose and the detector average pixel intensity.

17. The method of claim 12, wherein obtaining the normalized air map comprises dividing the calibration image data with the detector average pixel intensity.

18. The method of claim 12, wherein the calibration image data is obtained by adjusting the X-ray tube electrical parameter such that the calibration image data pixel values are around the middle of the dynamic range of the detector.

19. The method of claim 12, wherein the generating the air map is based on the following equation:

$$I_0(i,j) = D \times P \times \bar{a}_{i,j}^{\{kVp\}}$$

where $I_0(i, j)$ is the air map, D is the detector entrance dose, P is the detector average pixel intensity, (i, j) are the pixel coordinates, kVp is the X-ray tube electrical parameter, and is the normalized air map.

20. The method of claim 19, wherein reconstructing image of the object based on the air map and the object X-ray intensity comprises first determining the x-ray attenuation based on the air map and the measurement data related to the object.

* * * * *